(12) United States Patent
Elkhoury et al.

(10) Patent No.: US 11,933,776 B2
(45) Date of Patent: Mar. 19, 2024

(54) PRESSURE METER TESTING APPARATUS AND METHOD

(71) Applicant: Schlumberger Technology Corporation, Sugar Land, TX (US)

(72) Inventors: Jean E. Elkhoury, Cambridge, MA (US); Thomas Berard, Clamart (FR); Emilie Peyret, Bucharest (RO); Romain Prioul, Concord, MA (US); Vincenzo De Gennaro, Pau (FR)

(73) Assignee: Schlumberger Technology Corporation, Sugar Land, TX (US)

(*) Notice: Subject to any disclaimer, the term of this patent is extended or adjusted under 35 U.S.C. 154(b) by 0 days.

(21) Appl. No.: 17/457,756

(22) Filed: Dec. 6, 2021

(65) Prior Publication Data

US 2022/0196629 A1 Jun. 23, 2022

Related U.S. Application Data

(60) Provisional application No. 63/128,575, filed on Dec. 21, 2020.

(51) Int. Cl.
| | |
|---|---|
| *G01N 33/24* | (2006.01) |
| *E21B 33/124* | (2006.01) |
| *E21B 33/127* | (2006.01) |
| *E21B 47/003* | (2012.01) |
| *E21B 47/06* | (2012.01) |
| *E21B 49/00* | (2006.01) |
| *G01N 19/00* | (2006.01) |

(52) U.S. Cl.
CPC ......... *G01N 33/24* (2013.01); *E21B 33/1243* (2013.01); *E21B 33/127* (2013.01); *E21B 47/003* (2020.05); *E21B 47/06* (2013.01); *E21B 49/00* (2013.01); *E21B 49/006* (2013.01); *G01N 19/00* (2013.01)

(58) Field of Classification Search
CPC .... G01N 33/24; G01N 19/00; E21B 33/1243; E21B 33/127; E21B 47/003; E21B 47/06; E21B 49/00; E21B 49/006
See application file for complete search history.

(56) References Cited

U.S. PATENT DOCUMENTS

| | | | | |
|---|---|---|---|---|
| 4,423,625 | A | * | 1/1984 | Bostic, III ............ E21B 49/087 73/152.52 |
| 5,353,637 | A | * | 10/1994 | Plumb ................... E21B 49/008 166/308.1 |
| 5,784,333 | A | * | 7/1998 | Tang ........................ G01V 1/50 73/152.05 |

(Continued)

FOREIGN PATENT DOCUMENTS

| | | |
|---|---|---|
| EP | 2547865 B1 | 8/2018 |
| WO | 2020206303 A1 | 10/2020 |

OTHER PUBLICATIONS

Liu, (2005) Numerical Study of Reservoir Geomechanical Pressuremeter Testing under Anistropic In-situ Stresses, Univ. Alberta PMT tool, MSc. Thesis, Univ. Alberta 2015, (180 pages).

(Continued)

*Primary Examiner* — Ryan D Walsh
(74) *Attorney, Agent, or Firm* — Jeffrey D. Frantz

(57) ABSTRACT

Embodiments provide a pressure meter testing apparatus and method that allows operations/engineers the ability to determine in-situ stiffness values of geological stratum.

17 Claims, 14 Drawing Sheets

(56) References Cited

U.S. PATENT DOCUMENTS

| | | | |
|---|---|---|---|
| 6,092,416 A * | 7/2000 | Halford | E21B 49/10 166/264 |
| 2004/0237640 A1 | 12/2004 | Meister et al. | |
| 2009/0164128 A1 | 6/2009 | Tchakarov et al. | |
| 2010/0051347 A1* | 3/2010 | Tchakarov | E21B 49/06 175/50 |
| 2010/0206548 A1* | 8/2010 | Pisio | E21B 49/006 166/250.1 |
| 2012/0150515 A1* | 6/2012 | Hariharan | E21B 49/008 703/7 |
| 2015/0136388 A1 | 5/2015 | Fehr | |
| 2017/0204726 A1 | 7/2017 | Lecampion et al. | |
| 2018/0334903 A1* | 11/2018 | Lehr | E21B 47/06 |
| 2018/0355715 A1* | 12/2018 | Cour | E21B 49/082 |
| 2021/0172315 A1* | 6/2021 | Alruwaili | E21B 49/006 |
| 2021/0262343 A1 | 8/2021 | Dupont et al. | |

OTHER PUBLICATIONS

International Search Report and Written Opinion of PCT Application No. PCT/US2021/059615 dated Apr. 20, 2022, 10 pages.
International Preliminary Report on Patentability issued in the PCT Application No. PCT/US2021/059615 dated Jun. 29, 2023, 7 pages.

\* cited by examiner

PRESSURE METER TESTING APPARATUS AND METHOD

CROSS-REFERENCE TO RELATED APPLICATIONS

This Application claims priority to U.S. Provisional Patent Application Ser. No. 63/128,575, filed Dec. 21, 2020, entitled: "Pressure Meter Testing Apparatus and Method", and International Application PCT/US2021/059615, filed Nov. 17, 2021 which are incorporated herein in their entirety.

FIELD OF THE DISCLOSURE

Aspects of the disclosure relate to testing of geological stratum. More specifically, aspects of the disclosure relate to a pressure meter testing method and apparatus using packers installed within a wellbore.

BACKGROUND

Ascertaining geological stiffness is a difficult process for engineers. Current practices require extensive laboratory work that can increase the costs of a wellbore dramatically. Some wellbores, for example, wellbores that may have a marginal rate of economic return, may not be pursued at all, if stiffness values for the geological stratum are questionable.

Conventionally, testing of in-situ stiffness values in field geological stratum is not accomplished on a wide scale in the industry. The reasons for this are complex and are the result of drawbacks to current technologies used by oil field service companies. Typically, in the oil and gas industry, elastic properties are measured in situ with sonic logging tools (WL or LWD) that yield "dynamic" stiffnesses (also called moduli) from elastic-wave velocity and density. "Static" stiffnesses (or moduli) are obtained from laboratory stress-strain experiments and are not measured in situ. A difference between "dynamic" and "static" stiffnesses comes from the difference on deformation (strain) amplitude. Generally, for geomechanics application, "static" elastic values are what is needed for computational and application purposes. The conventional practice is to measure dynamic and static stiffness on core samples in the lab after the well has been drilled and build a dynamic-static correlation so that the dynamic sonic stiffness log can be transformed (or "corrected") to a static stiffness log for applications. One of the drawbacks for such conventional methods is that the lab measurements on core samples is expensive and may take weeks to months to accomplish. During that time, the cores become unconfined when taken out of the hole. At this point, the results are not necessarily representative of downhole conditions even if they are measured in a load cell under confinement. Conventionally, there are no methods to measure static elastic properties downhole, with the definition of elastic stiffness defined as:

Elastic stiffness=elastic modulus=elastic constant (units of Pascal)

Elastic compliance is the inverse of elastic stiffness

As will be understood by those of skill in the art, the different "stiffness" terms are loosely defined in mechanics wherein, for elasticity, stiffness is in units of Pascals.

One significant drawback to conventional apparatus is that such apparatus cannot be used effectively to determine the stiffness of a geological stratum. The inability to measure such parameters results in engineers making an "educated guess" as to this parameter. Such guesses/estimations must be made in a conservative fashion as failure to accurately represent such values can detrimentally affect the overall production of hydrocarbon bearing stratum.

For attempts at obtaining such values directly from field conditions, Engineers cannot accurately provide a surface test bed assembly that can be used in various field locations. Small modifications to a testing apparatus can impact resulting stiffness values on a large scale, therefore oil field service companies do not perform such tests as controls for such complicated testing are not present. Past attempts at obtaining stiffness values involve inflating an apparatus underground and trying to map a geological response to the inflation. Such prior attempts are very rudimentary and there is an established need to provide an apparatus and testing method that is more rigorous than the prior attempts.

Despite field induced complications as well as the potential for various test beds described above, there is a need to obtain sought after geological stiffness values.

There is a further need to provide an apparatus as well as methods that are easy to perform for field personnel such that stiffness values may be accurately derived.

There is a further need to provide apparatus and methods that do not have the drawbacks discussed above and wherein engineers can accurately ascertain stiffness values of the geological stratum adjacent to the wellbore.

There is a still further need to reduce economic costs associated with operations and apparatus.

There is a still further need to ascertain stiffness values, as defined and disclosed above as well as through later definition, for a geological stratum regardless of the type and number of packers, pump and associated stiffness of testing apparatus used.

SUMMARY

So that the manner in which the above recited features of the present disclosure can be understood in detail, a more particular description of the disclosure, briefly summarized below, may be had by reference to embodiments, some of which are illustrated in the drawings. It is to be noted that the drawings illustrate only typical embodiments of this disclosure and are therefore not to be considered limiting of its scope, for the disclosure may admit to other equally effective embodiments without specific recitation. Accordingly, the following summary provides just a few aspects of the description and should not be used to limit the described embodiments to a single concept.

In one non-limiting example embodiment, an arrangement is disclosed. The arrangement may comprise a packer system and a fluid delivery system connected to the packer system. The arrangement may also comprise at least one sensor system connected to the packer system and the fluid delivery system, wherein the at least one sensor system is configured to measure at least one of a pressure, a volume of fluid delivered to the packer system and a pressure experienced by the packer system. The arrangement may also comprise at least one computing system configured to obtained data related to the at least one of the pressure, the volume of fluid delivered to the packer system, and the pressure experienced by the packer system and calculate a geological stiffness factor.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the drawings. It is to be noted, however, that the appended drawings illustrate only typical embodiments of this disclosure and are therefore not to be considered limiting of its scope, for the disclosure may admit to other equally effective embodiments.

Figure 1:
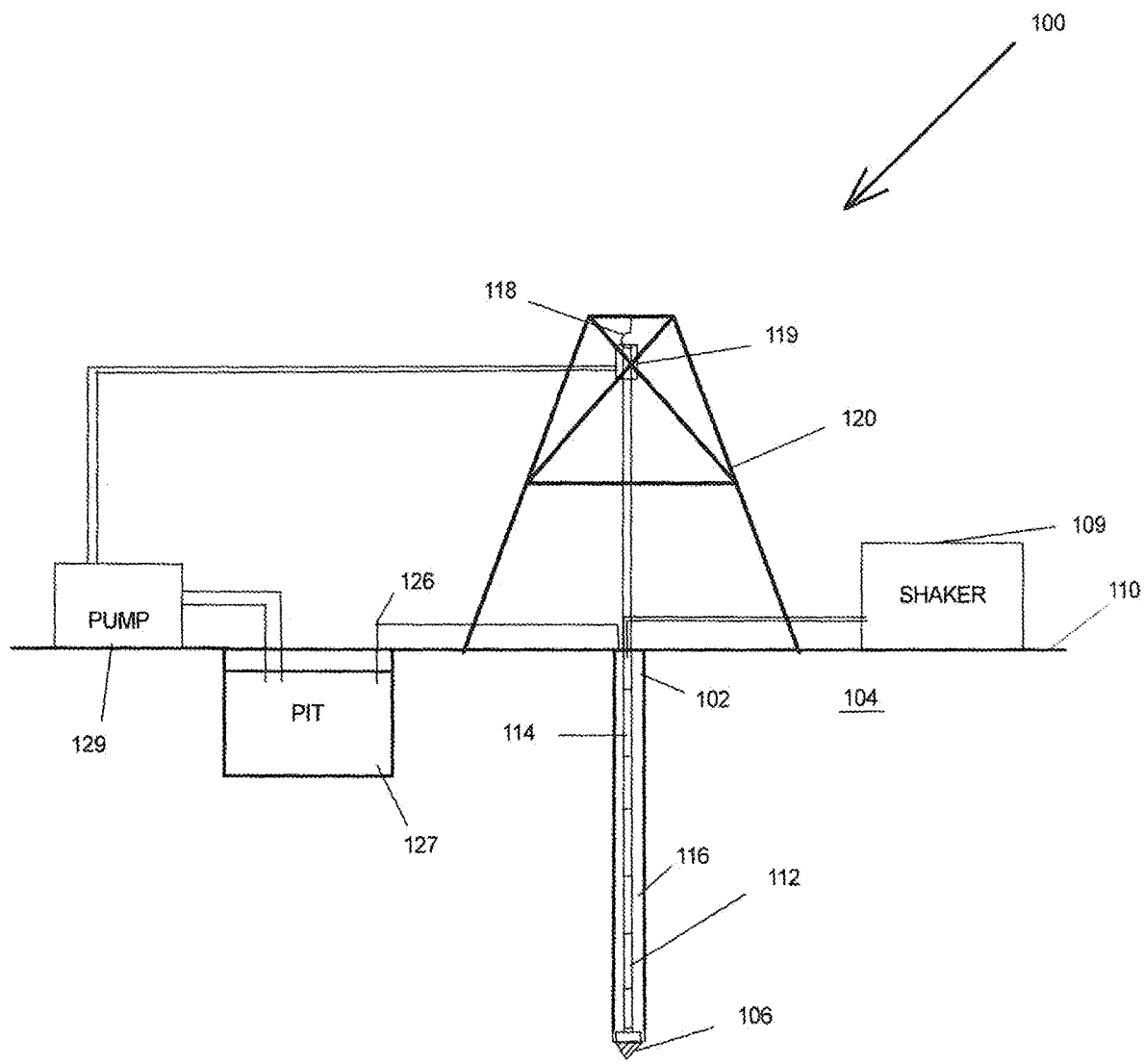
FIG. 1 is a drill rig performing a hydrocarbon recovery operation in one aspect of the disclosure.

To facilitate understanding, identical reference numerals have been used, where possible, to designate identical elements that are common to the figures ("FIGS"). It is contemplated that elements disclosed in one embodiment may be beneficially utilized on other embodiments without specific recitation.

DETAILED DESCRIPTION

In the following, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the claims except where explicitly recited in a claim. Likewise, reference to "the disclosure" shall not be construed as a generalization of inventive subject matter disclosed herein and should not be considered to be an element or limitation of the claims except where explicitly recited in a claim.

Although the terms first, second, third, etc., may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first", "second" and other numerical terms, when used herein, do not imply a sequence or order unless clearly indicated by the context. Thus, a first element, component, region, layer or section discussed herein could be termed a second element, component, region, layer or section without departing from the teachings of the example embodiments.

When an element or layer is referred to as being "on," "engaged to," "connected to," or "coupled to" another element or layer, it may be directly on, engaged, connected, coupled to the other element or layer, or interleaving elements or layers may be present. In contrast, when an element is referred to as being "directly on," "directly engaged to," "directly connected to," or "directly coupled to" another element or layer, there may be no interleaving elements or layers present. Other words used to describe the relationship between elements should be interpreted in a like fashion. As used herein, the term "and/or" includes any and all combinations of one or more of the associated listed terms.

Some embodiments will now be described with reference to the figures. Like elements in the various figures will be referenced with like numbers for consistency. In the following description, numerous details are set forth to provide an understanding of various embodiments and/or features. It will be understood, however, by those skilled in the art, that some embodiments may be practiced without many of these details, and that numerous variations or modifications from the described embodiments are possible. As used herein, the terms "above" and "below", "up" and "down", "upper" and "lower", "upwardly" and "downwardly", and other like terms indicating relative positions above or below a given point are used in this description to more clearly describe certain embodiments.

Embodiments for drilling of a wellbore will first be described. Once the wellbore is established, wireline operations may be used, in embodiments, as described in FIG. 2, to perform testing of geological stratum penetrated by the wellbore. Such testing will include pressure meter testing to determine a stiffness value for a geological stratum in question. Methods to perform operational activities can be controlled by a computer running predefined computer programs. An example computer is described in relation to FIG. 11. This computer may also help operations personnel control various method steps in the process of determining a stiffness value, as recited in FIG. 3. Although described as being associated with wireline operations described in FIG. 2, embodiments may be performed "while drilling", as described in FIG. 1 with modification to drilling equipment. As a result, the reader should not infer that measurements may only be obtained during wireline operations.

Referring to FIG. 1, a drilling rig 100 is illustrated. The purpose of the drilling rig 100 is to recover hydrocarbons located beneath the surface 110. Different stratum 104 may be encountered during the creation of a wellbore 102. In FIG. 1, a single stratum 104 layer is provided. As will be understood, multiple layers of stratum 104 may be encountered. Operators, therefore, need to assess the composition of the stratum 104 in order to maximize penetration of a drill bit 106 that will be used in the drilling process. The wellbore 102 is formed within the stratum 104 by a drill bit 106. In embodiments, the drill bit 106 is rotated such that contact between the drill bit 106 and the stratum 104 causes portions ("cuttings") of the stratum 104 to be loosened at the bottom of the wellbore 102. Differing types of drill bits 106 may be used to penetrate different types of stratum 104.

As the wellbore 102 penetrates further into the stratum 104, operators may add portions of drill string pipe 114 to form a drill string 112. As illustrated in FIG. 1, the drill string 112 may extend into the stratum 104 in a vertical orientation.

The drill bit 106 is larger in diameter than the drill string 112 such that when the drill bit 106 produces the hole for the wellbore 102, an annular space 116 is created between the drill string 112 and the inside face of the wellbore 102. This annular space provides a pathway for removal of cuttings from the wellbore 102.

The drilling fluids may be stored in a pit 127 located at the drill site. The pit 127 may have a liner to prevent the drilling fluids from entering surface groundwater and/or contacting surface soils.

Drilling fluid from the pit 127 is pumped by a mud pump 129 that is connected to a swivel 119. The drill string 112 is suspended by a drive 118 from a derrick 120. In the illustrated embodiment, the drive 118 may be a unit that sits atop the drill string 112 and is known in the industry as a "top drive".

Drilling fluid is provided to the drill string 112 through a swivel 119 suspended by the derrick 120. The drilling fluid exits the drill string 112 at the drill bit 106 and has several functions in the drilling process. The drilling fluid is used to cool the drill bit 106 and remove the cuttings generated by the drill bit 106. The drilling fluid with the loosened cuttings enter the annular area outside of the drill string 112 and travel up the wellbore 102 to a shaker 109.

The shaker 109 is configured to separate the cuttings from the drilling fluid. The cuttings, after separation, may be analyzed by operators to determine if the stratum 104 currently being penetrated has hydrocarbons stored within the stratum 104 level that is currently being penetrated by the drill bit 106. The drilling fluid is then recirculated to the pit 127 through the recirculation line 126.

As will be understood, different wellbores may have different constructions. For example, certain portions of the wellbore may have open sections, and certain sections may be cased hole section. Embodiments described herein may be used with different constructed wellbore embodiments and those discussed should not be considered limiting.

Figure 2:
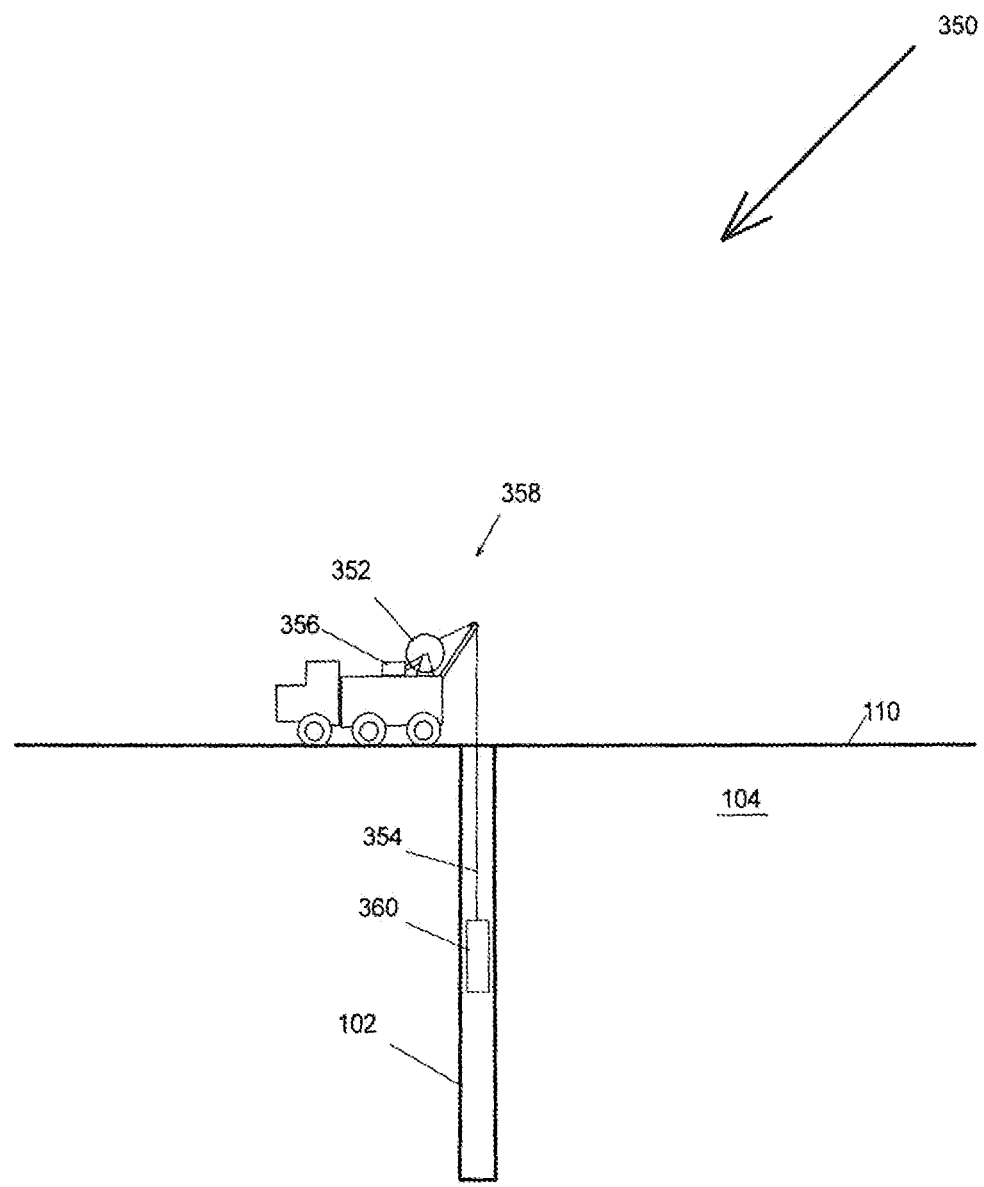
FIG. 2 is a cross-section of a wireline operation of the wellbore established in FIG. 1 conducting wireline formation tests on a formation.

Wireline operations are performed after the creation of the wellbore 102 as described in FIG. 1. Wireline operations may be accomplished to obtain subsurface petrophysical and geophysical data related to the geological stratum 104 encountered by the wellbore 102. Referring to FIG. 2, in these operations, a wireline truck 350 is provided. The wireline truck 350 is provided with a spool 352 that houses a cable 354. The cable 354 may be a single strand or multiple strand cable unit. The cable 354 is configured to allow sensors and equipment to be lowered into the wellbore 102 such that the sensors and equipment may conduct required surveys. The lowering action may be accomplished by a motor 356 that is connected to the spool 352. Within the wireline truck 350, an operator may activate and deactivate the motor 356 and control associated gearing to allow the spool 352 to unwind the cable 354 at a desired rate. Sensors 358 may be provided to ascertain the amount of cable 354 that has been unspooled to allow the operator to identify the location of equipment suspended by the cable 354.

Equipment supported by the cable 354 can be a single instrument package or multiple instrument packages. In the case of multiple instrument packages, such instrument packages may be modular such that different types of packages may be added together according to the needs of the operator. Different types of packages may include, but not be limited to:

Packer systems
Pressure meter testing systems
Nuclear measurement systems
Optical spectrometry systems
Pressure monitoring systems
Resistivity calculation systems
Sonic and ultrasonic tool systems
Borehole seismic tool systems
Nuclear magnetic resonance tool systems
Pressure control systems
Tractor and motion enhancement systems
Power Generation systems
Telemetry and Data recordation systems
Computing systems Generally, the different modular systems described above may be added together, as needed, to form a logging tool 360 that may be called or known as a sonde. The logging tool 360 is lowered into the wellbore 102 to a desired point in the geological stratum 104 and the appropriate system is actuated. The wireline operator may take sensor readings at one point or may take multiple readings while changing the elevation of the logging tool 360. The resulting string of measurements may be called a "log". Wireline operations may also be used in remediation of a wellbore 102 in order to increase production of hydrocarbons. Such operations, known as remediation or "workovers" may include augmenting existing wellbore 102 parameters. In embodiments herein, measurements may be made during times where sensors and equipment are non-moving. Such non-movement acquisition is defined as a "station" measurement as opposed to a "log" where data is acquired during movement of a tool.

In the instance of non-vertical wells, wireline operations may be augmented through the use of tractors that allow for the tools to reach more horizontally positioned portions of a wellbore. Such horizontal portions of a wellbore may be found, for example, in wells involving fracking operations where a "pay zone" is deposited horizontally parallel to the ground surface. To reach the near horizontal positions of such a wellbore, a tractor that grips the sides of the wellbore may be used to convey instrument packages to the desired position in the wellbore.

In the following description, description is provided related to measurements obtained during wireline operations generally performed, as described above. As will be understood, various changes and alterations may be accomplished during the attainment of the desired measurements, and as such, methods described should not be considered limiting.

In embodiments, formation stiffness is desired to be calculated through use of a wirelines apparatus described in relation to FIG. 2. Such calculations are performed through use of a pressure meter testing apparatus described later. Conventional apparatus and methods cannot accurately derive formation stiffness values in an economic manner. For purposes of definition, stiffnesses in units of Pascal/m3. This quantity is extracted from pressure-volume curve, that will be related to the shear modulus (or shear stiffness in Pascal) by multiplying the stiffness in Pa by a volume quantity in m3.

Three factors are provided herein to enable the use of pressure meter testing to obtain stiffness values for in-situ geological stratum. The first factor relates to hardware. Embodiments of the disclosure provide for specific hardware components that are used to accurately obtain stiffness values. These hardware components include a single packer system or multiple packers that are lowered into the wellbore in order to isolate a section of formation for testing. In one non-limiting embodiment, packers used in conjunction with pressure meter testing are relatively "stiff" compared to conventional packers. The use of packers that are "stiff" provide for an increased overall stiffness of the test bed apparatus (defined as all of the components used to conduct the test), thereby resulting in more accurate geological stiffness measurement values. It should be noted, however, that different types of packers may be used in conjunction with the remainder of the selected tools, and that stiffness values may be obtained from conventional or "non-stiff" packers. Experimental testing has identified that increasing the overall stiffness of the test bed apparatus results in superior calculated values. In embodiments, the packers used herein may be separate units from a sensor system that is used or the packers may have sensors as an integral part of the configuration.

A second factor provided herein relates to calibration of the test bed apparatus and wellbore undergoing testing. In embodiments, calibration occurs for a cemented or "cased" steel wellbore. As each field constructed wellbore can vary, knowledge of the actual thickness of the cementing project as well as the thickness and type of steel used in formation of the wellbore establishes a well-known assemblage of parameters that can be used in the third factor.

The third factor is interpretation of results obtained from the tested wellbore. Using the "known" wellbore construction values obtained in the second factor, values obtained during the testing regime described later can provide for derivation of geological stiffness values based upon the known or calibrated wellbore construction.

Figure 3:
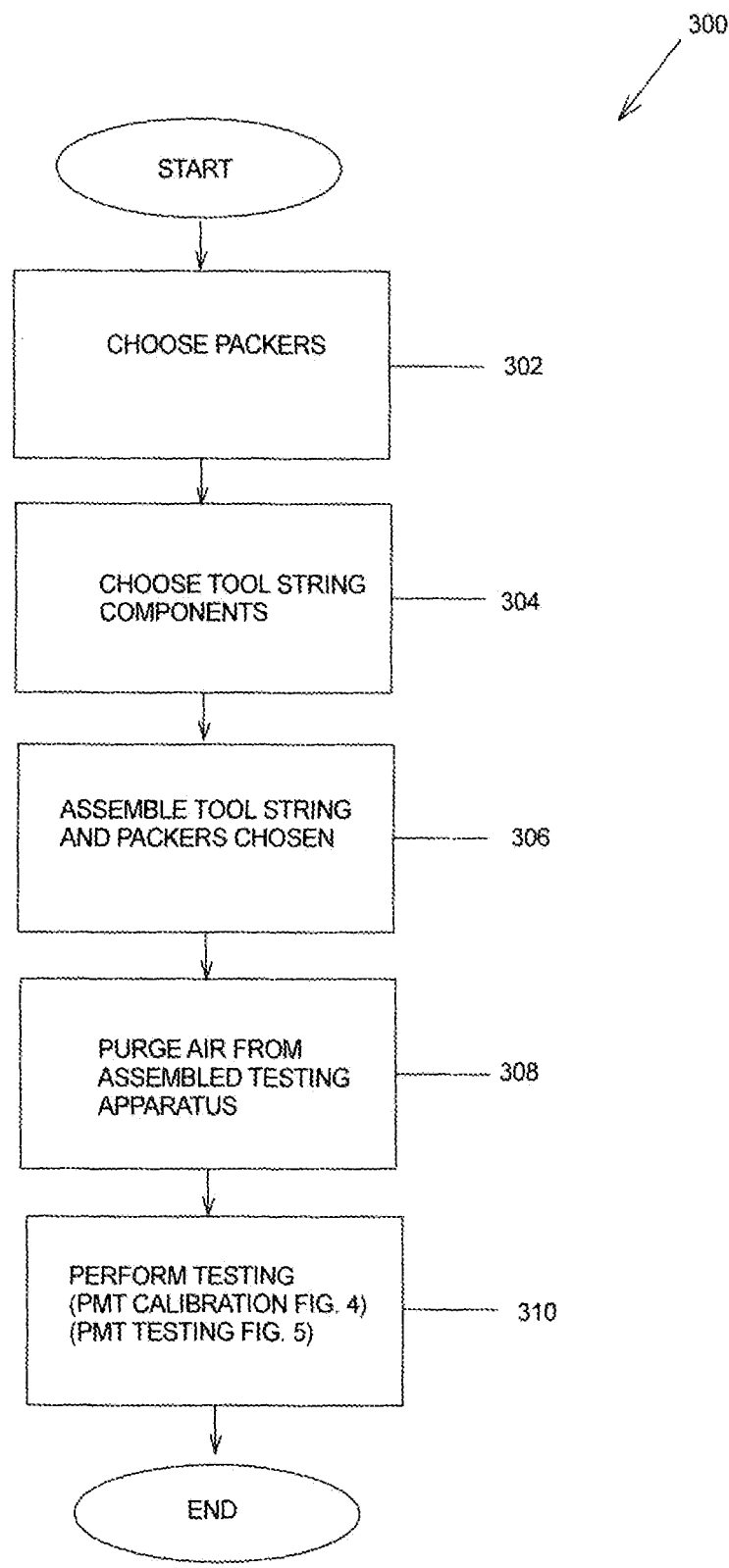
FIG. 3 is a method of performing a test on a geological stratum in accordance with one example embodiment of the disclosure.

Referring to FIG. 3, a method 300 for performing a test on a geological stratum is illustrated. The method 300 provides, at 302, selecting a type and number of packers that will be used in the test bed apparatus. In one example embodiment, two packers that have a greater stiffness compared to stiffness of conventional packers are chosen. Other embodiments may use conventional packers if an especially stiff test bed apparatus is not needed. At 302, a single packer may be specified for use with a "dummy" or "can" packer that is essentially a packer that is not expandable. The use of any number of packers should not be considered limiting. As by further definition, a single packer installation has one expandable packer with no "dummy" or "can" packer.

Further referring to FIG. 3, at 304, a tool string is chosen to interface with the packer(s) selected at 302. The tool string may include, for example, a pump, fluid delivery systems, valving systems, safety systems, sensor systems and control systems. As will be understood, different types of pumps may be selected, such as high volume-low pressure pumps, low volume-high pressure pumps, medium volume-medium pressure pumps and various combinations of the types described above. Fluid delivery systems may include piping to deliver a fluid, such as water or other non-compressible fluid, down to the packer/double packer configuration. The fluid can include, for example, tap water, filtered water, de-aired water, Glycerin, or other fluids. The piping may be made of different types of materials. Types of materials may include carbon steel or stainless steel, as non-limiting embodiments. Different geometries of pipe may be selected, including thin-walled piping/tubing to extra-heavy walled pipe. Selection of the different properties will allow for a relatively stiffer or weaker overall stiffness for the test bed apparatus. As will be understood, having prior knowledge of a range of packer stiffness that is available as well as having prior information on the formation, a recommendation of a suitable packer may be performed based upon the field and equipment limitations. Safety systems selected may allow for single or redundant/single failure proof designs to ensure proper testing actuation. In embodiments, different displacement units may be specified for use with the remainder of the tool string.

After selection of the components of the tool string and packers in steps 302 and 304, the tool string may be assembled at 306 and deployed into the wellbore. At 308, air is purged from the tool string assembled at 306. The purpose of purging the tool string of any air present allows for modulation of the fluids to the packers selected in step 302 to provide a true non-compressible status for the tool string. At 310, a test may be conducted with the tool string after purging of the air. Testing performed at 310 may be conducted in two parts, namely a PMT calibration portion and a PMT measurement portion. The PMT calibration portion is described in relation to FIG. 4. The PMT measurement portion is described in relation to FIG. 5.

Figure 4:
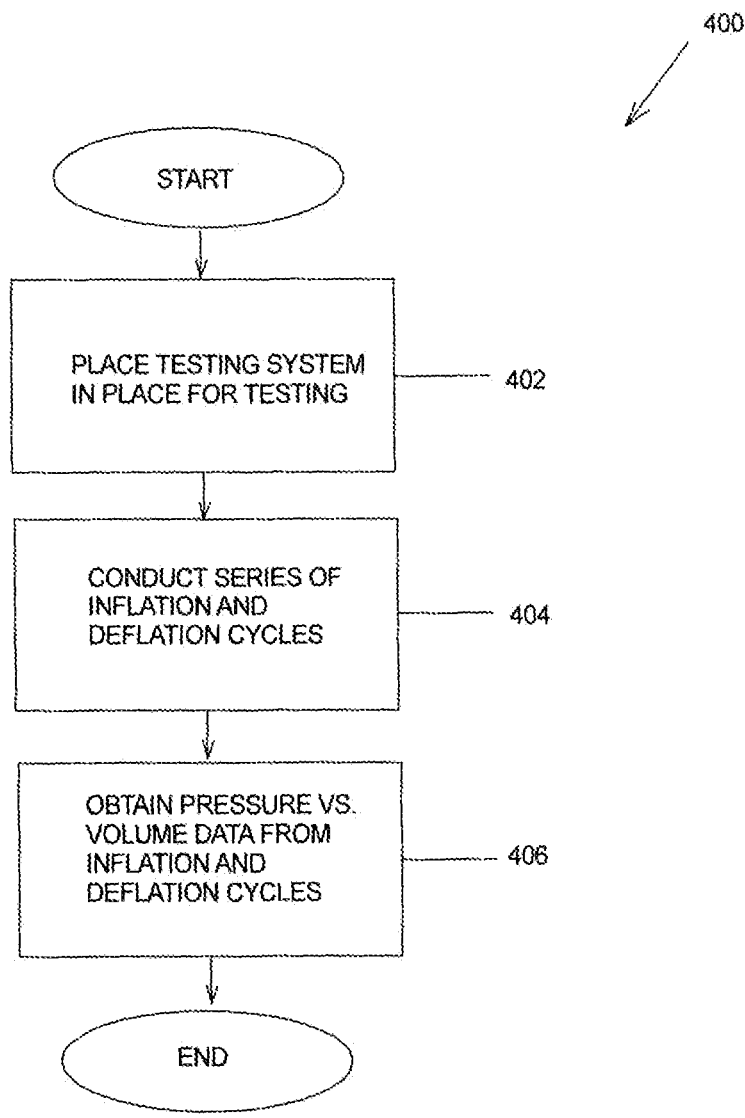
FIG. 4 is a method of performing the PMT calibration portion of the test on the geological stratum of FIG. 3.

Referring to FIG. 4, a calibration portion of the testing performed in FIG. 3 is illustrated. The calibration portion provides a method 400 that involves, at 402, placing the assembled testing apparatus assembled in 306 to a calibration testing position. In embodiments, placement of the apparatus deep within the borehole provides results that are acceptable. At 404, a series of inflation and deflation cycles are performed within the wellbore. Different inflation and deflation cycles may be used, with example alternatives described in FIGS. 6, 7 and 8. During the series of inflation and deflation cycles, pressure is measured as a function of injected volume at all points in the inflation and deflation cycle. At 406, the pressure vs. volume data obtained at 404 are processed to obtain a value of stiffness as a function of pressure or deformation or volume. In instances where the wellbore has a casing that is cemented in place and is well bonded, an effective casing stiffness can be inferred. This effective casing stiffness can be used to infer tool stiffness (pump, flow line+packer). As will be understood, various embodiments of the above may be accomplished. These embodiments may measure volume injected and/or measure cavity deformation. As will be further understood, embodiments described below relate to injected volumes and calculations based upon injected volumes, however, as will be understood by a person skilled in the art, cavity deformation may also be used.

In embodiments, effective casing stiffness is defined as $M_c$ and the measured stiffness in the casing as $M_{mc}$ from which the packer stiffness $M_s$, the stiffness of the hydraulic system (pump+flowline+packer+fluid) is defined from the equation below:

$$M_s = \frac{M_c M_{mc}}{M_c - M_{mc}} \qquad \text{EQUATION 1}$$

Figure 5:
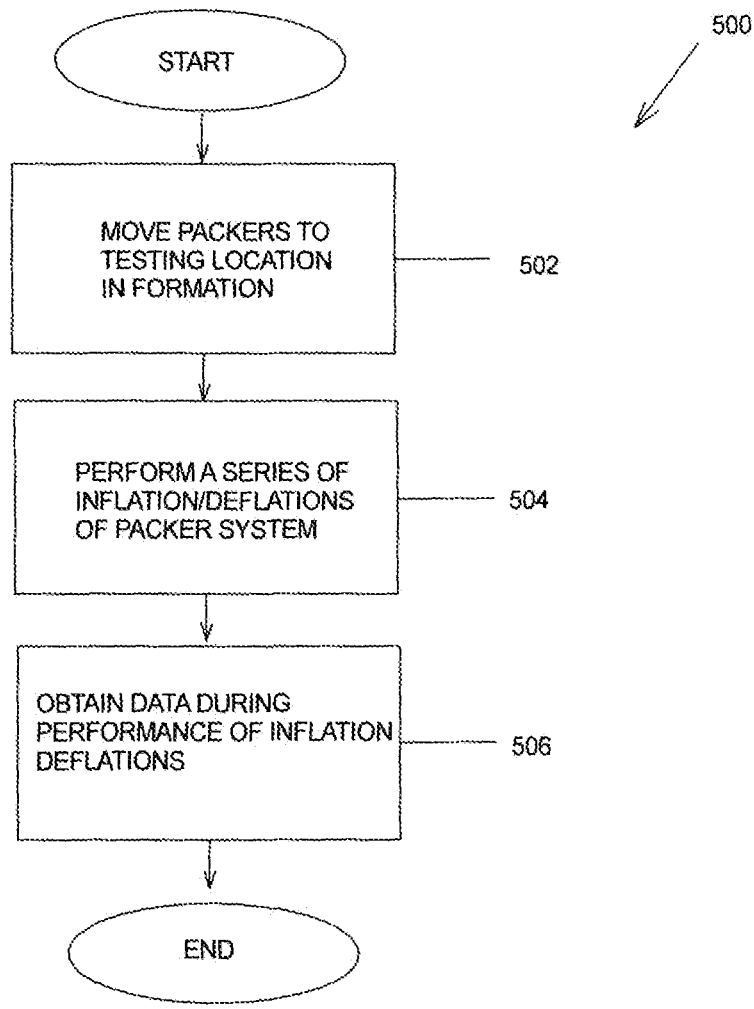
FIG. 5 is a method of performing the PMT measurement portion of the test on the geological stratum of FIG. 3.

Once $M_s$ has been calculated according to equation 1, the formation stiffness may be inferred from a PMT test conducted in FIG. 5.

In some instances, casing may not be used within a wellbore. Aspects of the disclosure may also be used in this instance. When casing is not present, calibration may occur in a very stiff portion of the formation where there is a known stiffness or where the stiffness can be correctly approximated. In instances where a very stiff portion of the formation is not available, embodiments provide for performing calibration in a portion of the wellbore that is the stiffest and then refer this stiffness of all other formations in reference to the chosen point of stiffness (in relative terms).

Referring to FIG. 5, pressure meter testing of the formation is described. As provided above, after conducting a calibration test in relation to FIG. 4, the pressure meter testing may be accomplished. In this method 500, the packer or series of packers may be moved to the target formation 502. At 504, a series of inflation and deflation protocols may be accomplished. Different protocols may be used, with non-limiting example protocols described in FIGS. 6, 7 and 8. At 506, during the series of inflation and deflation protocols, data on the pressures encountered and fluid volumes used are recorded.

The previously derived value $M_s$ of tool stiffness is recalled. The measured pressure injected volumes in the formation are processed and produce a measured stiffness in the formation $M_m$ according to the following equation. Mm is defined as measured stiffness in formation and $M_R$ is the formation stiffness Using the values $M_s$ and $M_m$ the formation stiffness $M_R$ may be calculated from equation 2.

$$M_R = \frac{M_s M_m}{M_s - M_m} \quad \text{EQUATION 2}$$

In addition to the above, a static in-situ shear modulus G may be obtained from the value $M_R$ using values of contact length L of a packer and borehole radius $r_b$ through the use of equation 3.

$$G = M_R \pi L r_b^2 \quad \text{EQUATION 3}$$

The static in-situ modulus G can be reported as a single value independent of pressure or a function of pressure which may be an indication of the specific mechanical properties of the target formation. Using the in-situ module G, the Young's modulus can be calculated from a known Poisson's ratio and vise-versa.

Processing of the data obtained from the field testing may be accomplished in the field, if desired. The basic processing consists of calculating the change in pressure as a function of the change in injected volume. That is the gradient of the pressure with respect of the injected volume. This is the stiffness and has units of pressure per unit of volume. In one example embodiment, reported values may be in values of $Pa/m^3$.

In embodiments, smoothing filters may be used for calculated values to eliminate distortions in the data. In one example embodiment, a moving average window may be used to eliminate noisy data. The size of the window may be selected according to the amount of data and the noise level as example factors.

In other example embodiments, curve fitting may be used. Example embodiments may include, but not be limited to:
Local gradient and moving average smoothing
Local polynomial fits of degree n (n=1, 2, 3, . . . ) and data range m
Savizky-Golay finite impulse response (RIR) smoothing filters
Smooth Spline After such fitting, the gradient (dP/dV) is performed on the fitted/smoother function. This will provide a smoother result.

Volume and pressure corrections may also be performed. In embodiments, the pressure (P) and injected volume (V) into the packer or packers may be accounted for in some embodiments. As will be understood, correction of data due to volume and pressure may be accomplished in some embodiments and not accomplished in others. For example, volume and pressure corrections may be insignificant to other sources of error, therefore volume and pressure corrections may be omitted. In some examples, sources of error may be minimized and the volume and pressure corrections may be more significant with respect to overall error. In these instances, volume and pressure corrections may be performed. Pressure and volume corrections may include error developed from the influence of inflating the packer, as there may be some pressure that is spent on inflating the packer due to packer inherent stiffness, therefore the amount of pressure being exerted upon the formation may be less. Such pressure and volume corrections may vary according to the size and type of packers used, as a non-limiting embodiment.

Figure 6:
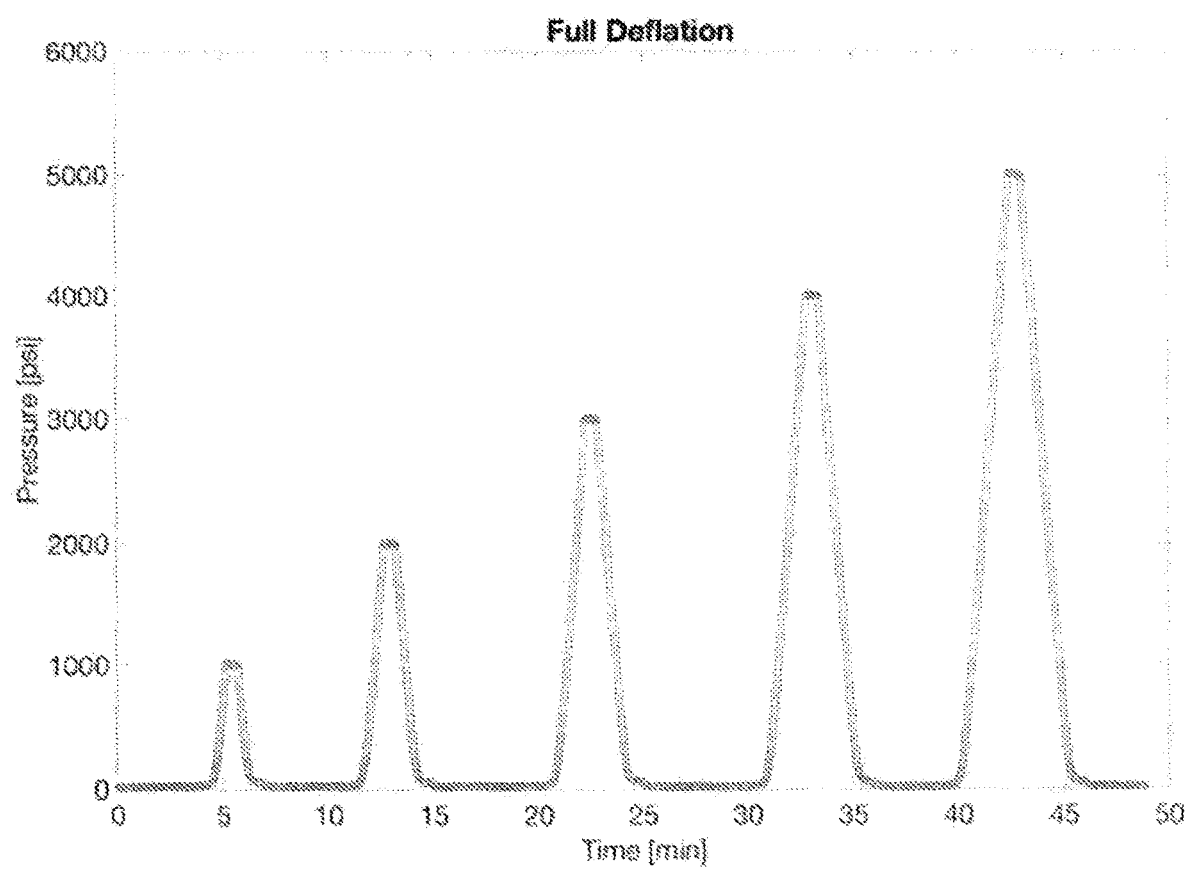
FIG. 6 is a graph of a full deflation, increasing pressure protocol that may be used with the method of performing the PMT calibration portion of FIG. 4 or PMT measurement portion of FIG. 5.

Referring to FIG. 6, a sample inflation protocol is illustrated. This protocol may be used in either calibration (FIG. 4) or testing (FIG. 5). As illustrated, the graph provides a plot of pressure over time. In the example embodiment, the graph provides pressure in pounds per square inch and the time axis provides time in minutes. As illustrated, pressure in the first step is raised to a value of 1000 psi, with following steps increasing pressure up to 2000 psi, 3000 psi, 4000 psi and 5000 psi. Deflation steps follow each of the inflation steps. Deflation steps may occur incrementally longer in time as the pressure increases. The protocol described in FIG. 6 provides a simple protocol that may be conducted in the field. This protocol may be performed prior to any sleeve fracturing within the wellbore. Furthermore, this protocol may provide a stiffness at lower pressure compared to other inflation protocols described below.

Figure 7:
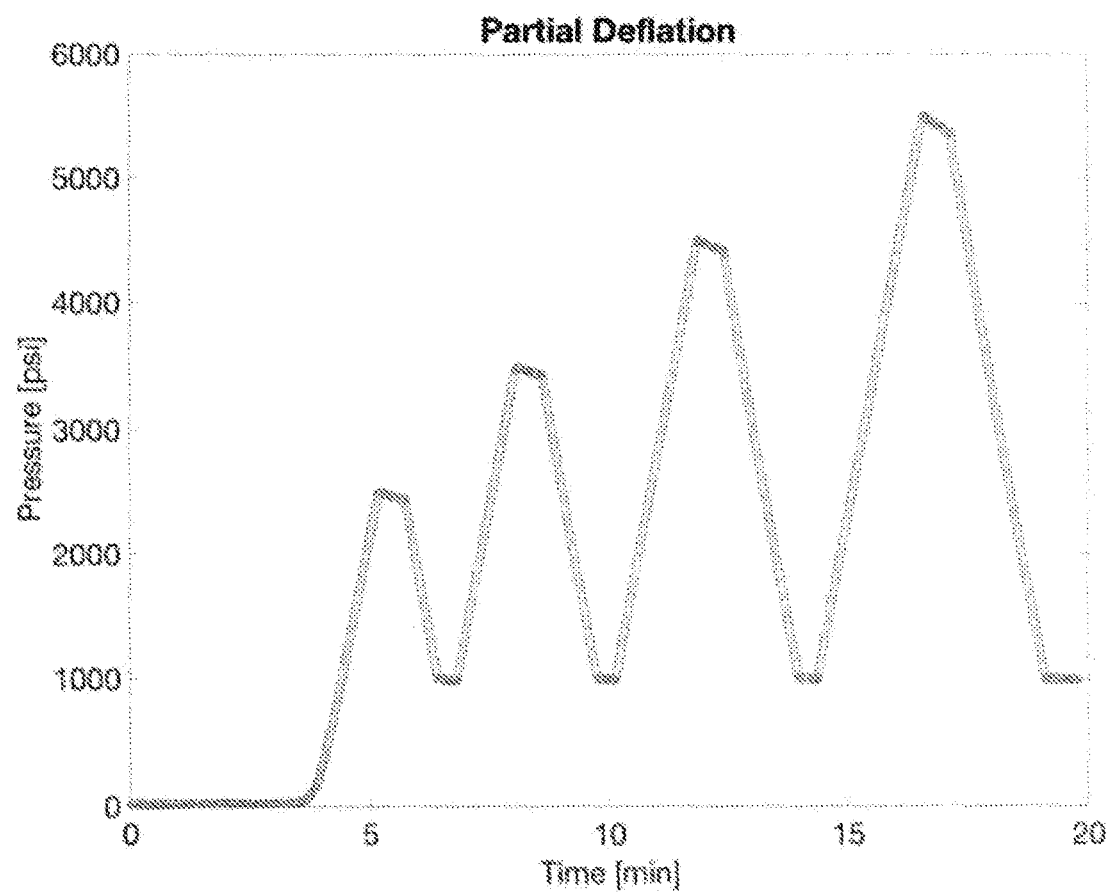
FIG. 7 is a second graph of constant partial deflation protocol that may be used when performing the PMT calibration portion of FIG. 4 or PMT measurement portion of FIG. 5.

FIG. 7 illustrates a second inflation protocol that may be used. This inflation protocol, similar to that in FIG. 6, may be used in either calibration or testing. As illustrated, the graph provides a plot of pressure over time. In the example embodiment, the graph provides pressure in pounds per square inch and the time axis provides time in minutes. As illustrated, pressure in the first step is raised to a value of 2500 psi followed by a partial deflation to 1000 psi. This is followed by a subsequent inflation to 3500 psi followed by a partial deflation 1000 psi. Each subsequent inflation may increase to 4500 psi and 5500 psi with deflations back to 1000 psi.

Figure 8:
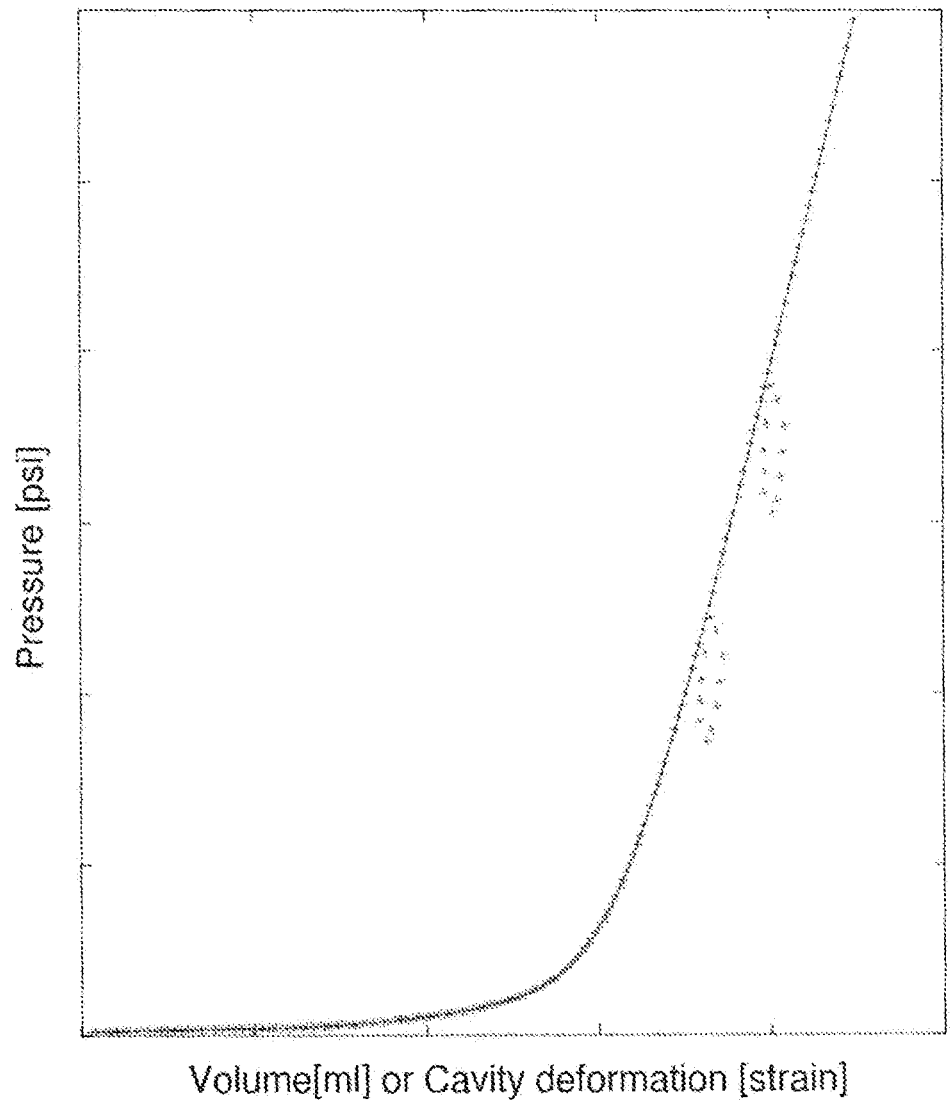
FIG. 8 is a third graph of increasing pressure with cycles protocol that may be used when performing the PMT calibration portion of FIG. 4 or PMT measurement portion of FIG. 5.

Referring to FIG. 8, a third inflation protocol is illustrated. As with the protocols described in relation to FIG. 6 and FIG. 7, the third inflation protocol may be used in relation to both calibration and testing. As illustrated, the graph provides a plot of pressure over strain (actually pressure vs time and strain vs time are used for a pressure-strain plot). In the example embodiment, the graph provides pressure in pounds per square inch and the time axis provides time in minutes. As illustrated, pressure may be increased over time with the results recorded.

Figure 9:
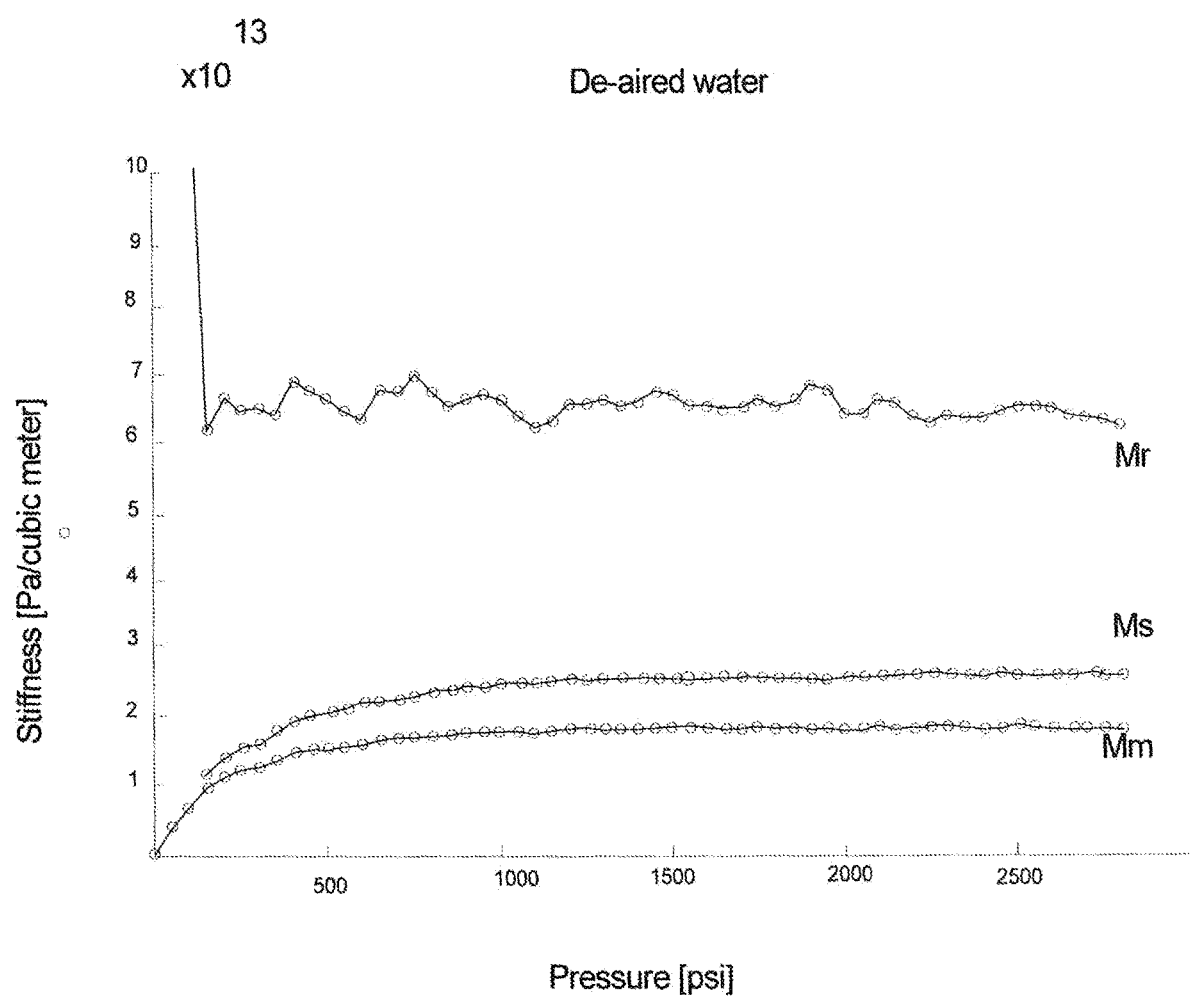
FIG. 9 is a graph of three stiffnesses as a function of pressure.

Referring to FIG. 9, a graph of stiffness as a function of pressure is illustrated. Three data sets are illustrated in the graph. These data sets include, descending from the top of the graph, sample stiffness $M_R$, packer stiffness $M_s$ and measured stiffness $M_m$. Tests were accomplished with de-aired water, however, other suitable fluids can be used, such as tap water, distilled water, Glycerin, or the like, used as the working fluid (pumped fluid). Sample stiffness $M_R$ were calculated using a length (L) of 1.82 inches and a length to diameter ratio L/D=2.43. For FIG. 9, packer properties used included steel pipe with an ID=0.762 inches and OD=0.999 inches. For measured stiffness values, a LEXAN cylinder with an ID=0.755 inches and an OD=5.098 inches. As can be seen from the plots, sample stiffness can vary somewhat over the range of pressures tested from 0 psi to approximately 2750 psi. Packer stiffness values, after initial inflation occurring at approximately 500 psi, are relatively constant at $2.5 \times 10^{13}$ Pa/m$^3$. Such values are expected as, after inflation, packer stiffness should be constant or approximately constant in value over the pressure range. Measured stiffness follows a similar pattern to that of packer stiffness, wherein after full inflation of the packer(s) at 500 psi, values are consistent over the range of pressure.

Aspects of the disclosure provided in FIG. 9 indicate that lower pressure values may be successfully used in field testing. Such lower required field pressure values are significant as overstressing of the formation does not occur. As testing may be conducted at lower pressures, valuable field time is saved performing such tests compared to higher pressure and longer interval tests.

Figure 10:
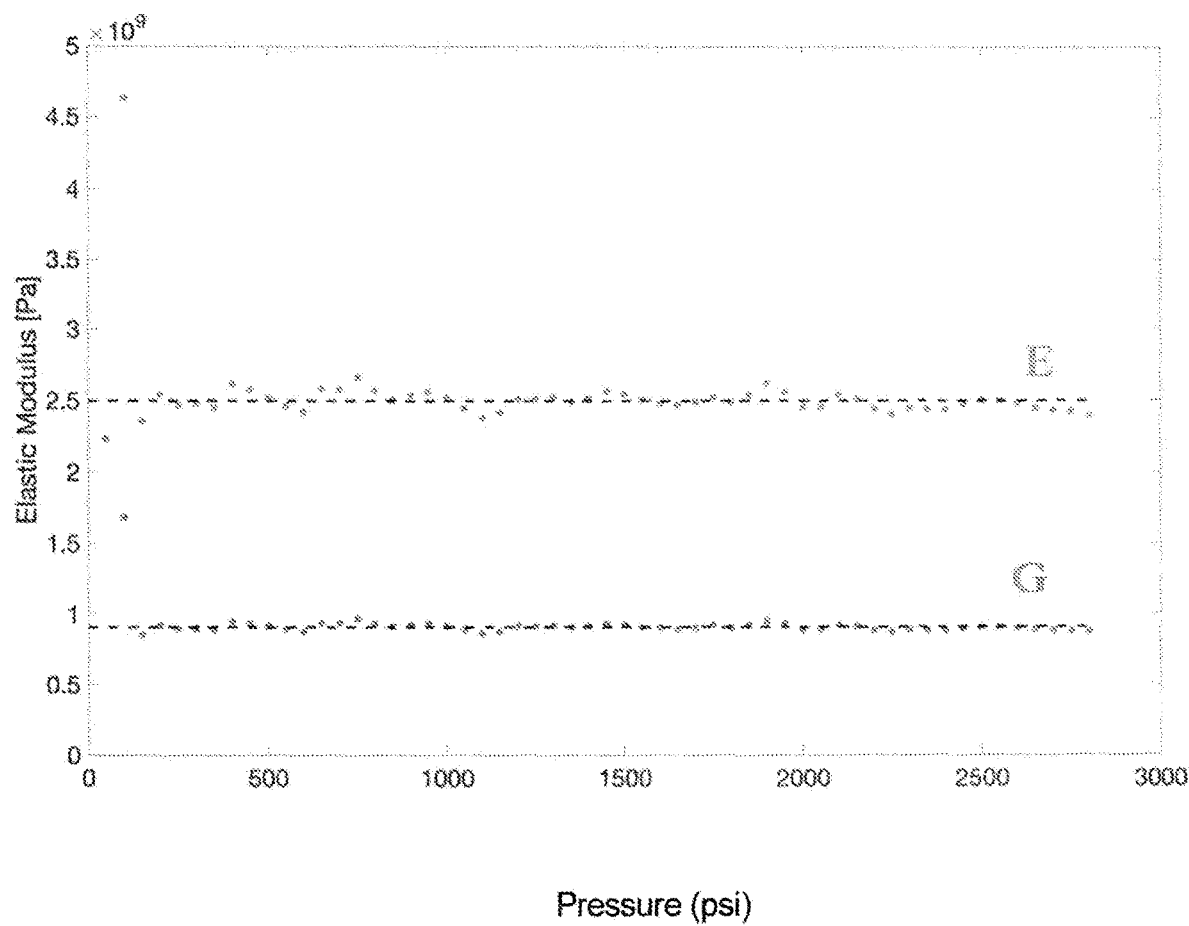
FIG. 10 is a graph of elastic modulus, Young's and shear moduli, as a function of pressure.
Figure 12:
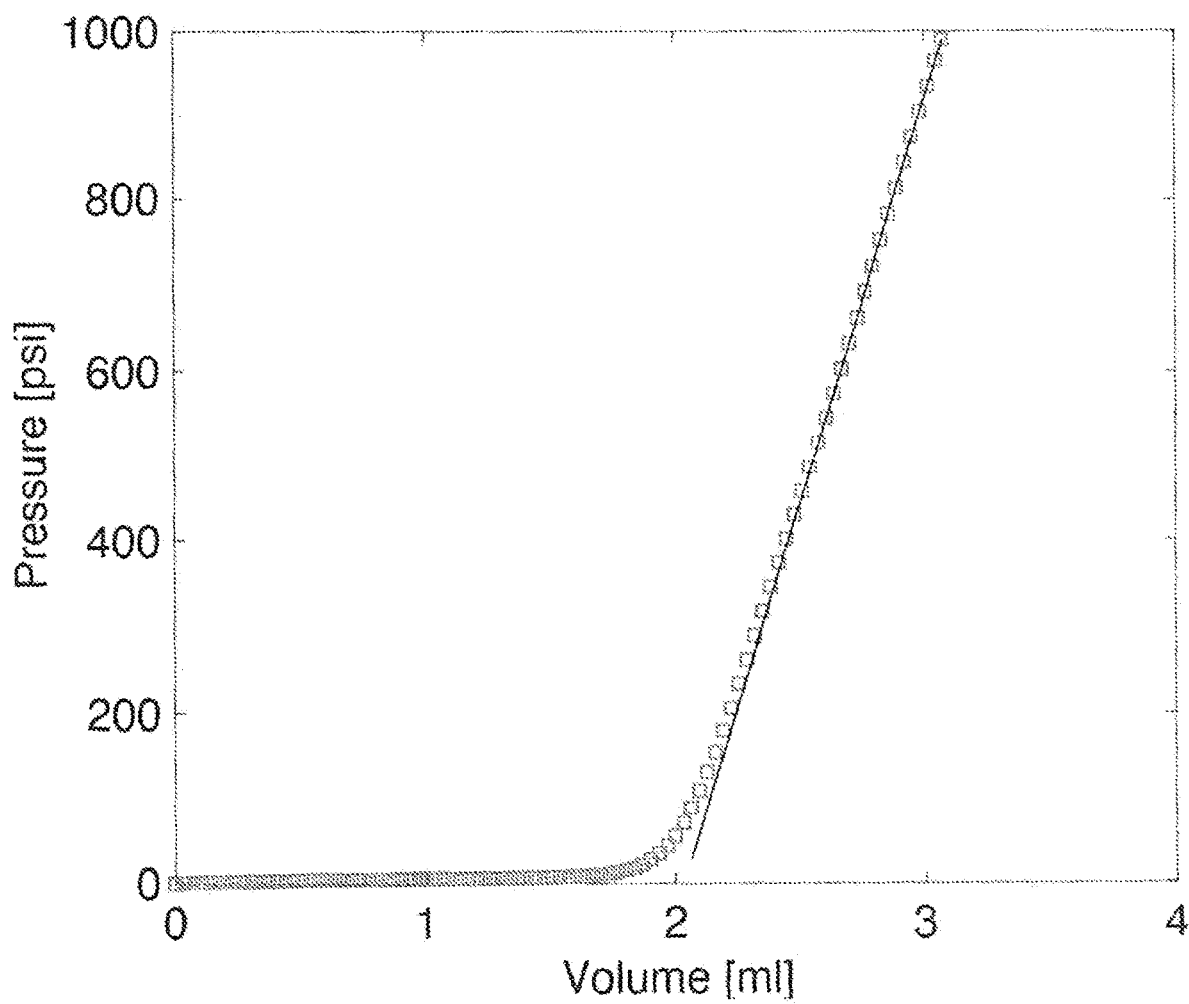
FIG. 12 is a graph of pressure vs. volume pertaining to analysis performed by the method embodiment described.
Figure 13:
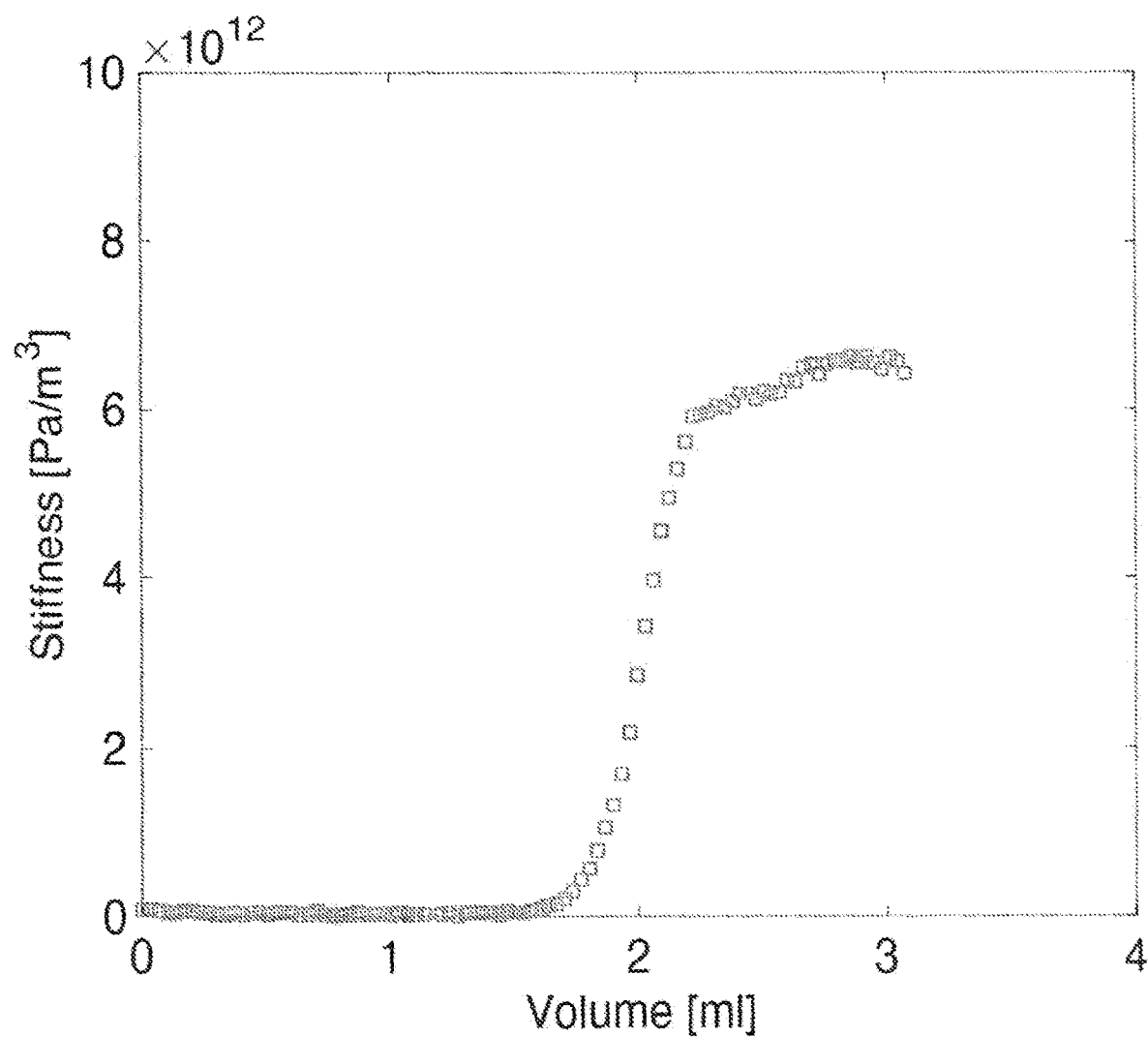
FIG. 13 is a graph of stiffness vs. volume pertaining to analysis performed by the method embodiment described.
Figure 14:
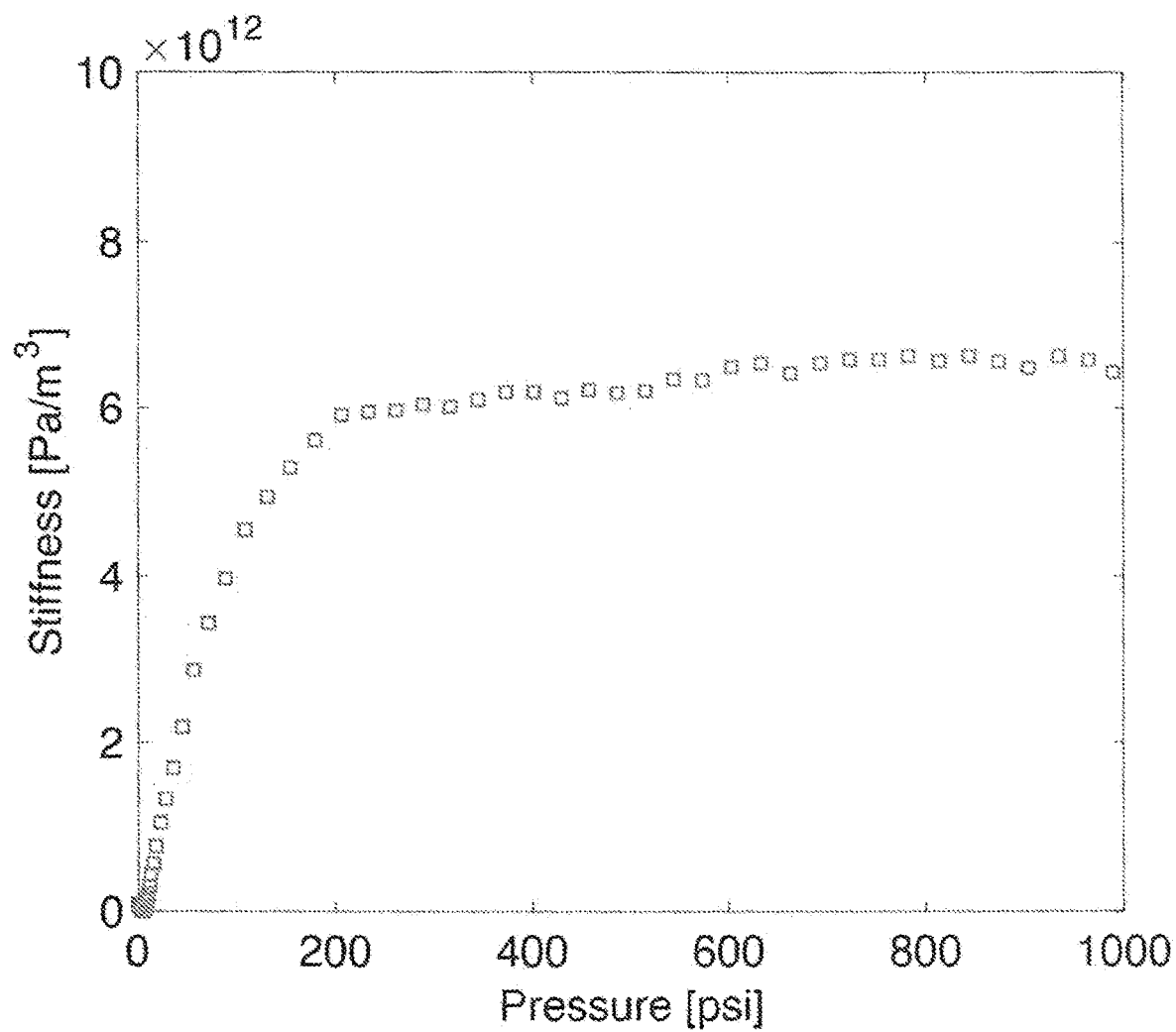
FIG. 14 is a graph of stiffness vs. pressure pertaining to analysis performed by the method embodiment described.

Referring to FIG. 10, a graph of elastic moduli vs. pressure is illustrated. The elastic moduli are in units of Pa, while the pressure is in pounds per square inch. Values for static elastic moduli are presented at the top of the graph, while value G represents static in-situ shear modulus, obtained from Eq 3 using measured $M_R$ and known L and $r_b$. Young's modulus can be derived from known or assumed Poisson's ratio. As can be seen, values of both E and G are consistent along the tested pressures from 150 to 2750 psi, indicating that lower pressure tests yield results similar to that of higher test pressures. Referring to FIGS. 12 to 14, differing graphs of laboratory data have been used to verify the accuracy of the methods described.

Aspects of the disclosure described above provide methods that may be performed to achieve a stated goal of determining geological stiffness values as well as controlling components described in the specification. In some embodiments, the methods described may be performed by circuits and/or computers that are configured to perform such tasks.

Figure 11:
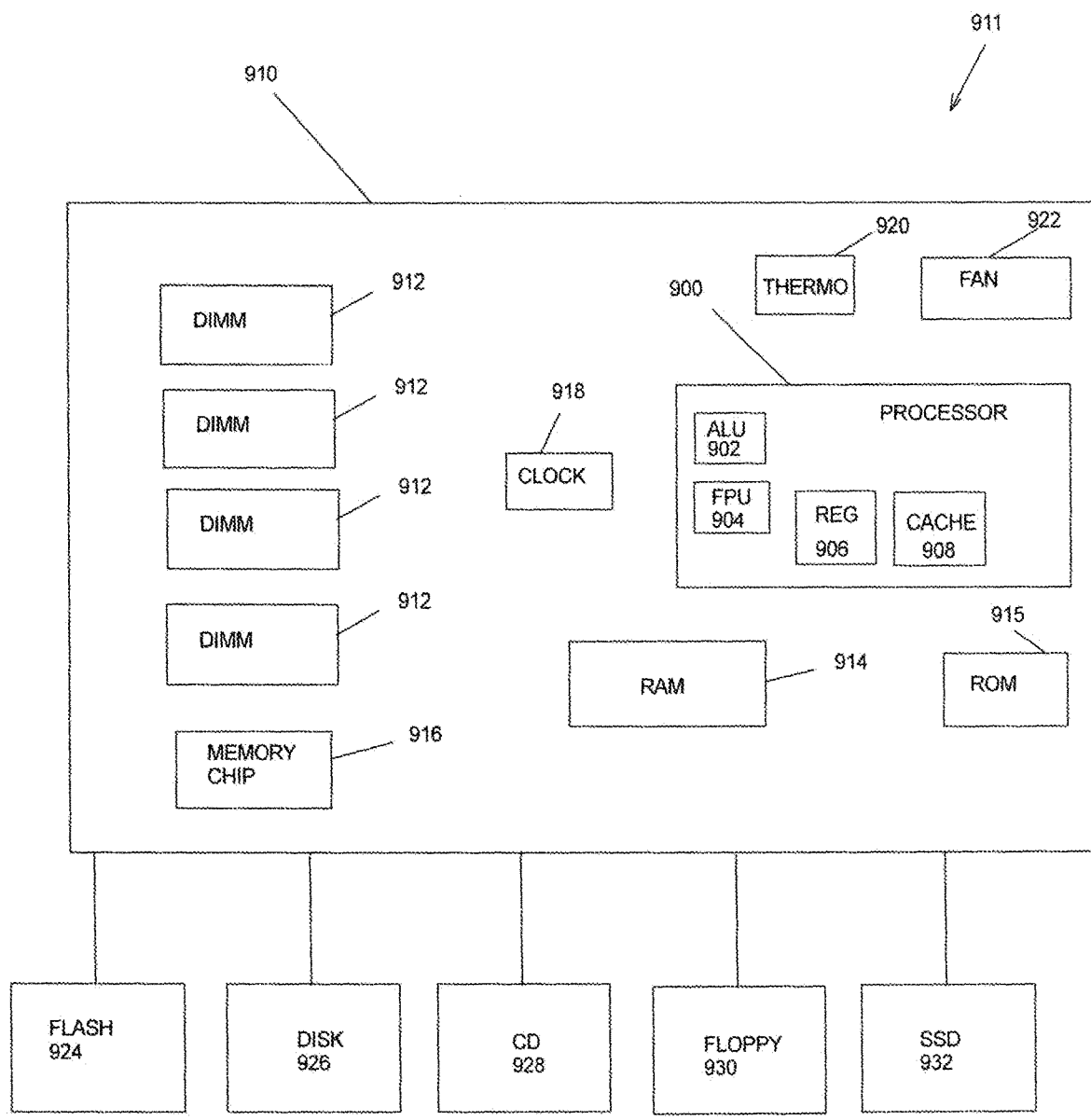
FIG. 11 is a computer apparatus used in performing a method described in FIG. 3 and controlling apparatus for the wireline operations of FIG. 2.

In such embodiments, referring to FIG. 11, a computing apparatus 911 used in the control of equipment of FIG. 1 and FIG. 2 is illustrated. The computing apparatus 911 may also be configured to perform operations steps described in FIGS. 3, 4 and 5. In FIG. 11, a processor 900 is provided to perform computational analysis for instructions provided. The instruction provided, code, may be written to achieve the desired goal and the processor 900 may access the instructions. In other embodiments, the instructions may be provided directly to the processor 900.

In other embodiments, other components may be substituted for generalized processors. These specifically designed components, known as application specific integrated circuits ("ASICs") are specially designed to perform the desired task. As such, the ASIC's generally have a smaller footprint than generalized computer processors. The ASIC's, when used in embodiments of the disclosure, may use field programmable gate array technology, that allows a user to make variations in computing, as necessary. Thus, the methods described herein are not specifically held to a precise embodiment, rather alterations of the programming may be achieved through these configurations.

In embodiments, when equipped with a processor 900, the processor 900 may have arithmetic logic unit ("ALU") 902, a floating point unit ("FPU") 904, registers 906 and a single or multiple layer cache 908. The arithmetic logic unit 902 may perform arithmetic functions as well as logic functions. The floating point unit 904 may be a math coprocessor or numeric coprocessor to manipulate numbers far efficiently and quickly than other types of circuits. The registers 906 are configured to store data that will be used by the processor 900 during calculations and supply operands to the arithmetic logic unit 902 and store the result of operations. The single or multiple layer caches 908 are provided as a storehouse for data to help in calculation speed by preventing the processor 900 from continually accessing random access memory ("RAM") 914.

Aspects of the disclosure provide for the use of a single processor 900. Other embodiments of the disclosure allow the use of more than a single processor. Such configurations may be called a multi-core processor where different functions are conducted by different processors to aid in calculation speed. In embodiments, when different processors are used, calculations may be performed simultaneously by different processors, a process known as parallel processing.

The processor 900 may be located on a motherboard 910. The motherboard 910 is a printed circuit board that incorporates the processor 900 as well as other components helpful in processing, such as memory modules ("DIMMS") 912, random access memory 914, read only memory, non-volatile memory chips 916, a clock generator 918 that keeps components in synchronization, as well as connectors for connecting other components to the motherboard 910. The motherboard 910 may have different sizes according to the needs of the computer architect. To this end, the different sizes, known as form factors, may vary from sizes from a cellular telephone size to a desktop personal computer size. The motherboard 910 may also provide other services to aid in functioning of the processor 900, such as cooling capacity. Cooling capacity may include a thermometer 920 and a temperature controlled fan 922 that conveys cooling air over the motherboard 910 to reduce temperature.

Data stored for execution by the processor 900 may be stored in several locations, including the random access memory 914, read only memory 915, flash memory 924, computer hard disk drives 926, compact disks 928, floppy disks 930 and solid state drives 932. For booting purposes, data may be stored in an integrated chip called an EEPROM, that is accessed during start-up of the processor 900. The data, known as a Basic Input/Output System ("BIOS"), contains, in some example embodiments, an operating system that controls both internal and peripheral components.

Different components may be added to the motherboard or may be connected to the motherboard to enhance processing. Examples of such connections of peripheral components may be video input/output sockets, storage configurations (such as hard disks, solid state disks, or access to cloud based storage), printer communication ports, enhanced video processors, additional random access memory and network cards.

The processor and motherboard may be provided in a discrete form factor, such as personal computer, cellular telephone, tablet, personal digital assistant or other component. The processor and motherboard may be connected to other such similar computing arrangement in networked form. Data may be exchanged between different sections of the network to enhance desired outputs. The network may be a public computing network or may be a secured network where only authorized users or devices may be allowed access.

As will be understood, method steps for completion may be stored in the random access memory, read only memory, flash memory, computer hard disk drives, compact disks, floppy disks and solid state drives.

Different input/output devices may be used in conjunction with the motherboard and processor. Input of data may be through a keyboard, voice, Universal Serial Bus ("USB") device, mouse, pen, stylus, Firewire, video camera, light pen, joystick, trackball, scanner, bar code reader and touch screen. Output devices may include monitors, printers, headphones, plotters, televisions, speakers and projectors.

In one non-limiting embodiment, a method is disclosed. The method may comprise selecting a packer system for testing a geological formation and choosing components for testing the geological formation. The method may further comprise assembling the tool string components and the packer system into a test bed assembly. The method may also comprise positioning the test bed assembly tool string components into a wellbore placed within the geological formation. The method may further comprise performing a pressure meter test on the formation.

In one non-limiting embodiment, a method may be performed wherein the performing the pressure meter test has a calibration portion and a testing portion.

In one non-limiting embodiment, a method may be performed wherein the calibration portion comprises: placing the assembled tool string into a calibration testing position; conducting a series of inflation and deflation cycles with the tool string; obtaining data of pressure and volume from the series of inflation and deflation cycles; and processing the obtained data of pressure and volume to obtain a stiffness value of the tool string.

In one non-limiting embodiment, a method may be performed wherein at least one volume and pressure correction is performed on the data of pressure and volume from the series of inflation and deflation cycles.

In one non-limiting embodiment, a method may be performed wherein at least one volume and pressure correction is performed on the data of pressure and volume from the second series of inflation and deflation cycles.

In one non-limiting embodiment, a method may be performed wherein the testing portion comprises placing the assembled tool string into a testing position, conducting a second series of inflation and deflation cycles with the tool string, obtaining data of pressure and volume from the second series of inflation and deflation cycles and processing the obtained data of pressure and volume to obtain a stiffness value of the formation.

In one non-limiting embodiment, the method may be performed wherein smoothing filters are used on the obtained data of pressure and volume from at least one of the series of inflation and deflation cycles and the second series of inflation and deflation cycles.

In one non-limiting embodiment, the method may be performed wherein the choosing the components for testing the geological formation includes selecting a pump and a fluid delivery system.

In one non-limiting embodiment, the method may be performed wherein the calibration portion is performed in a section of the wellbore with a casing.

In one non-limiting embodiment, the method may be performed wherein the calibration portion is performed in a section of the wellbore without a casing.

In one non-limiting embodiment, the method may be performed wherein the method is performed on wireline.

In one non-limiting embodiment, the method may be performed while drilling.

In one non-limiting embodiment, the method may be performed wherein the selecting the packer system for testing the geological formation includes selecting a double packer arrangement.

In one non-limiting embodiment, the method may be performed wherein the selecting the packer system of testing the geological formation includes selecting a single packer arrangement.

In one non-limiting example embodiment, an arrangement is disclosed. The arrangement may comprise a packer system and a fluid delivery system connected to the packer system. The arrangement may also comprise at least one sensor system connected to the packer system and the fluid delivery system, wherein the at least one sensor system is configured to measure at least one of a pressure, a volume of fluid delivered to the packer system and a pressure experienced by the packer system. The arrangement may also comprise at least one computing system configured to obtained data related to the at least one of the pressure, the volume of fluid delivered to the packer system and the pressure experienced by the packer system and calculate a geological stiffness factor.

In another example embodiment, the arrangement may be configured wherein the fluid delivery system includes a pump.

In another example embodiment, the arrangement may be configured wherein the fluid delivery system further comprises a piping system.

In another example embodiment, the arrangement may be configured wherein the packer system is configured with a single inflatable packer.

In another example embodiment, the arrangement may be configured wherein the packer system is configured with at least one non-inflatable packer.

In another example embodiment, the arrangement may be configured wherein the arrangement is configured to be delivered by a wireline.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may be varied in many ways. Such variations are not to be regarded as a departure from the disclosure, and all such modifications are intended to be included within the scope of the disclosure.

While embodiments have been described herein, those skilled in the art, having benefit of this disclosure, will appreciate that other embodiments are envisioned that do not depart from the inventive scope. Accordingly, the scope of the present claims or any subsequent claims shall not be unduly limited by the description of the embodiments described herein.

What is claimed is:
1. A method, comprising:
assembling a logging tool for measuring a pressure within a portion of a wellbore, wherein the logging tool comprises one or more sensors and one or more packers;

positioning the logging tool into the portion of the wellbore, wherein the one or more packers are positioned in a section of a geological formation associated with the portion of the wellbore;

purging air from the logging tool; and performing a pressure meter test on the section of the geological formation, wherein the pressure meter test comprises:

performing a series of inflation and deflation cycles within the section of the geological formation; and receiving a plurality of pressure and volume measurements associated with the section of the geological formation from the one or more sensors during the series of inflation and deflation cycles.

2. The method according to claim 1, wherein the performing the pressure meter test comprises a calibration portion and a testing portion.

3. The method according to claim 2, wherein the calibration portion comprises:

placing the logging tool into a calibration testing position;

conducting a first series of inflation and deflation cycles with the logging tool;

obtaining data of pressure and volume measurements associated with the first series of inflation and deflation cycles; and processing the obtained data of pressure and volume measurements to obtain a stiffness value of the logging tool.

4. The method according to claim 3, wherein at least a portion of the data of pressure and volume measurements corresponds to a proxy for a cavity deformation.

5. The method according to claim 3, wherein at least one volume and pressure correction is performed on the data of pressure and volume measurements based on the first series of inflation and deflation cycles.

6. The method according to claim 3, wherein at least one volume and pressure correction is performed on the data of pressure and volume measurements based on a second series of inflation and deflation cycles.

7. The method according to claim 3, further comprising:

using smoothing filters on the obtained data of pressure and volume measurements associated with the first series of inflation and deflation cycles.

8. The method according to claim 2, wherein the testing portion comprises:

placing the logging tool into a testing position;

conducting a one of the series of inflation and deflation cycles with the logging tool;

obtaining data of pressure and volume measurements associated with the one of the series of inflation and deflation cycles; and processing the obtained data of pressure and volume measurements to obtain a stiffness value of the section of the geological formation.

9. The method according to claim 2, wherein the calibration portion is performed in the portion of the wellbore with a casing.

10. The method according to claim 2, wherein the calibration portion is performed in the portion of the wellbore without a casing.

11. The method according to claim 1, further comprising pumping one or more fluids into the wellbore via a pump.

12. The method according to claim 1, wherein the method is performed on wireline.

13. The method according to claim 1, wherein the method is performed while drilling.

14. The method according to claim 1, wherein the one or more packers for testing the section of the geological formation comprises a double packer arrangement.

15. The method according to claim 1, wherein the one or more packers for testing the section of the geological formation comprises a single packer arrangement.

16. A method, comprising assembling a logging tool for measuring a pressure within a portion of a wellbore, wherein the logging tool comprises one or more sensors and one or more packers;

positioning the logging tool into the portion of the wellbore, wherein the one or more packers are positioned in a section of a geological formation associated with the portion of the wellbore;

purging air from the logging tool;

performing a pressure meter test on the section of the geological formation, wherein the pressure meter test comprises:

performing a series of inflation and deflation cycles within the section of the geological formation; and receiving a plurality of pressure and volume measurements associated with the section of the geological formation from the one or more sensors during the series of inflation and deflation cycles;

calculating a geological stiffness factor based on the plurality of pressure and volume measurements; and estimating an elastic shear modulus based on the calculated geological stiffness factor.

17. The method according to claim 16, wherein the estimating the elastic shear modulus is performed as a function of the pressure.

\* \* \* \* \*